(12) United States Patent
Toriyama et al.

(10) Patent No.: US 12,366,813 B2
(45) Date of Patent: Jul. 22, 2025

(54) ELECTROPHOTOGRAPHIC PHOTORECEPTOR, PROCESS CARTRIDGE AND IMAGE-FORMING APPARATUS INCLUDING ELECTROPHOTOGRAPHIC PHOTORECEPTOR

(71) Applicant: SHARP KABUSHIKI KAISHA, Sakai (JP)

(72) Inventors: Kohichi Toriyama, Sakai (JP); Kenta Yoshida, Sakai (JP)

(73) Assignee: SHARP KABUSHIKI KAISHA, Sakai (JP)

(*) Notice: Subject to any disclaimer, the term of this patent is extended or adjusted under 35 U.S.C. 154(b) by 560 days.

(21) Appl. No.: 17/839,406

(22) Filed: Jun. 13, 2022

(65) Prior Publication Data

US 2022/0413403 A1 Dec. 29, 2022

(30) Foreign Application Priority Data

Jun. 28, 2021 (JP) .................................. 2021-106866

(51) Int. Cl.
*G03G 5/047* (2006.01)
*C07D 471/06* (2006.01)
(Continued)

(52) U.S. Cl.
CPC .......... *G03G 5/047* (2013.01); *C07D 471/06* (2013.01); *G03G 5/0655* (2013.01); *G03G 21/1803* (2013.01)

(58) Field of Classification Search
CPC .. G03G 5/047; G03G 5/0655; G03G 21/1803; C07D 471/06
See application file for complete search history.

(56) References Cited

U.S. PATENT DOCUMENTS 3,839,034 A 10/1974 Wiedemann
3,871,882 A 3/1975 Wiedemann
(Continued)

FOREIGN PATENT DOCUMENTS

JP S49-048334 A 5/1974
JP H10-048856 A 2/1998
(Continued)

OTHER PUBLICATIONS

Dr. Masashi Mamada et al., Benzimidazole Derivatives: Synthesis, Physical Properties, and n-Type Semiconducting Properties, Sep. 8, 2014, Chemistry A European Journal, vol. 20, Issue 37, pp. 11835-11846 (Year: 2014).*

*Primary Examiner* — Peter L Vajda
*Assistant Examiner* — Jenna Kuipers
(74) *Attorney, Agent, or Firm* — ScienBiziP, P.C.

(57) ABSTRACT

The present disclosure provides an electrophotographic photoreceptor including, on a conductive base, at least a photoreceptive layer or alternatively at least the photoreceptive layer and a protective layer laminated on the photoreceptive layer, in which both or either one of the photoreceptive layer and the protective layer contains a perimidine compound represented by general formula (I):

(Continued)

[Formula 1]

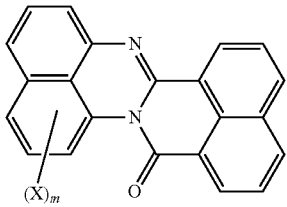

(I)

(wherein X represents hydrogen atom, an alkyl group having 1 to 6 carbon atoms, or an alkoxy group having 1 to 6 carbon atoms, and m represents an integer of 1 to 6).

7 Claims, 4 Drawing Sheets

(51) Int. Cl.
  *G03G 5/06* (2006.01)
  *G03G 21/18* (2006.01)

(56) References Cited

U.S. PATENT DOCUMENTS

| | | |
|---|---|---|
| 3,888,665 A | 6/1975 | Wiedemann |
| 3,973,959 A | 8/1976 | Rochlitz et al. |
| 5,952,139 A | 9/1999 | Takeuchi et al. |
| 10,488,770 B2 * | 11/2019 | Kuroiwa .............. G03G 5/0542 |
| 2010/0178074 A1 | 7/2010 | Nakatake et al. |

FOREIGN PATENT DOCUMENTS

| | | | |
|---|---|---|---|
| JP | H10-228121 A | | 8/1998 |
| JP | 2001-501667 A | | 2/2001 |
| JP | 2006-310278 A | | 11/2006 |
| JP | 2010-164639 A | | 7/2010 |
| JP | 2012103333 A | * | 5/2012 |
| JP | 2016-143024 A | | 8/2016 |

* cited by examiner

ELECTROPHOTOGRAPHIC PHOTORECEPTOR, PROCESS CARTRIDGE AND IMAGE-FORMING APPARATUS INCLUDING ELECTROPHOTOGRAPHIC PHOTORECEPTOR

BACKGROUND OF THE INVENTION

Field of the Invention

The present disclosure relates to an electrophotographic photoreceptor, and relates to a process cartridge and an image-forming apparatus that include the electrophotographic photoreceptor. More specifically, the present disclosure relates to an electrophotographic photoreceptor capable of suppressing damages to a photoreceptive layer due to external light, preventing deterioration of electric properties during repeated use, and continuously providing a good image quality, and relates to a process cartridge and an image-forming apparatus that include the electrophotographic photoreceptor.

Description of the Background Art

Recently, organic photoreceptors (hereinafter, also referred to as "electrophotographic photoreceptors" or simply "photoreceptors") using an organic photoconductive material have been widely used as an electrophotographic photoreceptor.

However, organic photoreceptors have a problem of light resistance concerning deterioration of the photoreceptive layer due to light. Generally, the photoreceptor is used in a light-shielded state inside an image-forming apparatus such as a copier and a laser printer and is not exposed to external light such as fluorescent lamp light. However, when assembling the machine (image-forming apparatus) or exchanging the photoreceptor, for example, if the photoreceptor is taken out from the machine due to paper jam, the photoreceptor is exposed to external light. Since an intensity of external light is extremely stronger than an intensity of the exposure light for image formation in the machine, the photoreceptor is severely damaged when exposed to external light, resulting in problems on image formation in some cases.

Thus, various efforts have been made as solutions for the above problems.

For example, JP H10-048856 A proposes a photoreceptor containing a fluorene compound having a specific structure and a compound having a maximum absorption wavelength at 380 to 480 nm, JP 2016-143024 A proposes a photoreceptor having a photoreceptive layer containing a benzophenone-based ultraviolet (UV) absorber having an absorption wavelength at 280 to 380 nm, and JP 2012-103333 A proposes a photoreceptor having a photoreceptive layer containing a light-absorbing compound having at least one maximum absorbance value in a range of 420 to 520 nm.

SUMMARY OF THE INVENTION

In the above prior arts, a light-absorbing compound having an absorbance at specific wavelengths and a UV absorber are added to the photoreceptive layer of the photoreceptor to reduce light damages to the photoreceptor, but these added compounds significantly deteriorate the electric properties of the photoreceptor during repeated use, resulting in problems causing fogging and decreasing an image density.

Thus, an object of the present disclosure is to provide an electrophotographic photoreceptor capable of suppressing damages to a photoreceptive layer due to external light, preventing deterioration of electric properties during repeated use, and continuously providing a good image quality, and provide a process cartridge and an image-forming apparatus that include the electrophotographic photoreceptor.

As a result of extensive studies to solve the above problems, the inventors have found that an electrophotographic photoreceptor capable of suppressing damages to a photoreceptive layer due to external light, preventing deterioration of electric properties during repeated use, and continuously providing a good image quality can be provided by adding a certain perimidine compound to both or either one of the photoreceptive layer and a protective layer of the photoreceptor, and therefore a process cartridge and an image-forming apparatus that include the electrophotographic photoreceptor can be provided. This finding has led to the completion of the present disclosure.

Thus, the present disclosure provide an electrophotographic photoreceptor including, on a conductive base, at least a photoreceptive layer or alternatively at least the photoreceptive layer and a protective layer laminated on the photoreceptive layer, in which
both or either one of the photoreceptive layer and the protective layer contains a perimidine compound represented by general formula (I):

[Formula 1]

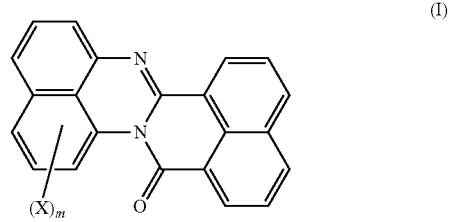

(wherein X represents hydrogen atom, an alkyl group having 1 to 6 carbon atoms, or an alkoxy group having 1 to 6 carbon atoms, and m represents an integer of 1 to (6).

In addition, the present disclosure provides an image-forming apparatus including at least the aforementioned electrophotographic photoreceptor, an electrifies for electrifying the electrophotographic photoreceptor, an exposer for exposing the electrified electrophotographic photoreceptor to form an electrostatic latent image, a developer for developing the electrostatic latent image formed by the exposure to form a toner image, a transferer for transferring the toner image formed by the development onto a recording medium, a fuser for fusing the transferred toner image onto the recording medium to form an image, a cleaner for removing and recovering a toner remaining on the electrophotographic photoreceptor, and a charge eliminator for eliminating surface charges remaining on the electrophotographic photoreceptor.

Furthermore, the present disclosure provides a process cartridge including at least one selected from the aforementioned electrophotographic photoreceptor, an electrifier for electrifying the electrophotographic photoreceptor, a developer for developing an electrostatic latent image formed by exposure to form a toner image, and a cleaner for removing a toner remaining on the electrophotographic photoreceptor.

The present disclosure makes it possible to provide an electrophotographic photoreceptor capable of suppressing damages to a photoreceptive layer due to external light, preventing deterioration of electric properties during repeated use, and continuously providing a good image quality, and provide a process cartridge and an image-forming apparatus that include the electrophotographic photoreceptor.

The aforementioned perimidine compound can absorb external light in the entire wavelength range of 480 to 600 nm and does not absorb light in a wavelength range of 600 to 800 e.g. an exposure light or a charge-eliminating light such as a laser of an image-forming apparatus, and therefore the perimidine compound is considered to be capable of suppressing (reducing) damages to the photoreceptive layer due to external light without impairing the exposure light or the charge-eliminating light. In addition, the perimidine compound does not deteriorate the electric properties of the photoreceptor during repeated use.

In the present disclosure, since damages to the photoreceptor due to external light is suppressed, the process cartridge equipped with the photoreceptor is easy to handle.

The above prior arts neither describe nor suggest the perimidine compound.

Damages to the photoreceptor due to external light such as a fluorescent lamp and an LED occur when external light penetrates a charge transporting layer and acts on a charge generating substance to cause charge trapping. General fluorescent lamps have light wavelength components at around 440 nm, 490 nm, 550 nm, 580 nm, and 620 nm, and white LEDs have light wavelength components at around 460 nm and 500 nm to 700 nm, and therefore, when these lights penetrate the charge transporting layer, these lights act on the charge generating material and generate a charge trap.

FIG. 4 presents an absorption spectrum of the perimidine compound represented by general formula (I) according to the present disclosure, which shows absorption in a wide range of 480 to 600 nm. It is considered that when the perimidine compound is added to the charge transporting layer or the protective layer, the perimidine compound functionally serves as a light absorbing compound, and thereby the light wavelength components can effectively block the action on the charge generating substance.

In addition, the light wavelength components at 600 to 800 nm must be permeable because the light wavelength components are used for an LED or laser beam for forming an electrostatic latent image by exposing a photoreceptor and an LED for eliminating surface charges remaining in the photoreceptor, or the like. Since the perimidine compound represented by general formula (I) according to the present disclosure does not show absorption at 600 800 nm, the perimidine compound is considered to be considerably preferable because of little adverse effects on the electric properties.

The photoreceptor according to the present disclosure exerts the aforementioned effects better, when any one of the following conditions (1) to (6) is satisfied.

(1) The perimidine compound is a compound in which the substituent X represents hydrogen atom and the exponent m represents 6 in general formula (I).
(2) The photoreceptive layer is a laminated photoreceptive layer in which a charge generating layer containing a charge generating substance and a charge transporting layer containing a charge transporting substance are sequentially laminated from a side of a conductive base, where the charge transporting layer contains the perimidine compound.
(3) A content of the perimidine compound is 0.05 to 1.5% by mass based on the total solid content of the charge transporting layer.
(4) The charge transporting layer has a film thickness of 18 to 42 μm.
(5) A content of the perimidine compound is 0.3 to 7% by mass based on the total solid content of the protective layer.
(6) The protective layer has a film thickness of 3 to 7 μm.

DESCRIPTION OF THE PREFERRED EMBODIMENTS (1) Electrophotographic Photoreceptor

A photoreceptor according to the present disclosure includes, on a conductive base, at least a photoreceptive layer or alternatively at least the photoreceptive layer and a protective layer laminated on the photoreceptive layer, in which both or either one of the photoreceptive layer and the protective layer contains a perimidine compound represented by general formula (I) (hereinafter, also referred to as the perimidine compound according to the present disclosure):

[Formula 2]

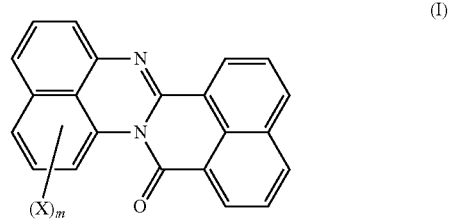

(I)

(wherein X represents hydrogen atom, an alkyl group having 1 to 6 carbon atoms, or an alkoxy group having 1 to 6 carbon atoms, and m represents an integer of 1 to 6).

Hereinafter, (1) a structure and constituent materials the photoreceptor will he explained, and (2) an image-forming apparatus and (3) a process cartridge that include the photoreceptor will be explained.

Photoreceptor

The photoreceptor according to the present disclosure includes, on the conductive base, at least a photoreceptive layer or alternatively at least the photoreceptive layer and a protective layer laminated on the photoreceptive layer.

Hereinafter, photoreceptors according to the present disclosure will be explained with reference to the figures, but the present disclosure is not limited to these photoreceptors.

The photoreceptor according to present disclosure may include an undercoat layer between the conductive base and the photoreceptive layer, and may include the protective layer on the photoreceptive layer i.e. the charge transporting layer, as described below.

Figure 1:
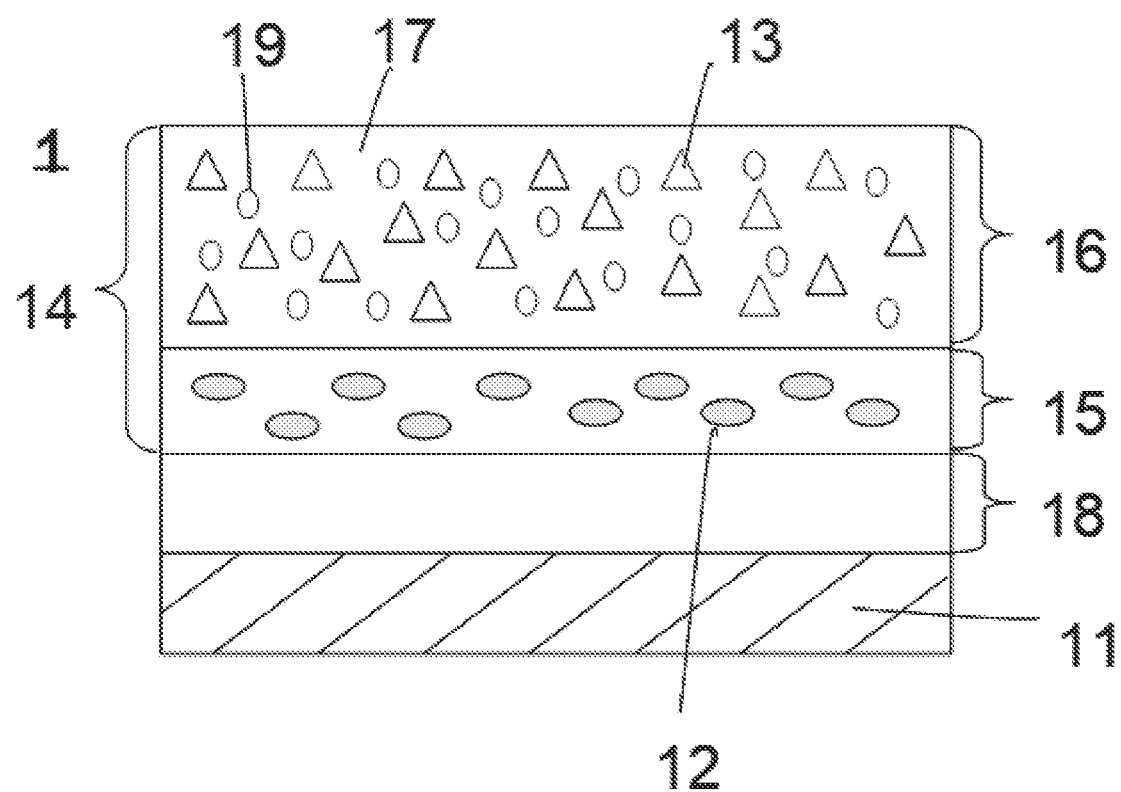
FIG. 1 is a schematic cross-sectional view illustrating a configuration of a main part of a photoreceptor 1 according to the present disclosure.

FIG. 1 is a schematic cross-sectional view illustrating a configuration of a main part of a photoreceptor 1 according to the present disclosure. A photoreceptor 1 is a laminated photoreceptor (also referred to as "function-separable type photoreceptor") that has a laminated-structural photoreceptive layer (also referred to as "laminated photoreceptive layer", "function-separable type photoreceptive layer") 14, in which an undercoat layer 18 is disposed on a conductive base 11, on which a charge generating layer 15 containing a charge generating substance 12, a charge transporting layer 16 containing a charge transporting substance 13, a binder resin 17 for bonding the charge transporting substance 13, and perimidine compound 19 according to the present disclosure are laminated in this order.

The photoreceptive layer of the photoreceptor according to the present disclosure is a laminated photoreceptive layer in which the charge generating layer containing the charge generating substance and the charge transporting layer containing the charge transporting substance are sequentially laminated from the side of the conductive base. Preferably, the charge transporting layer contains the perimidine compound.

Figure 2:
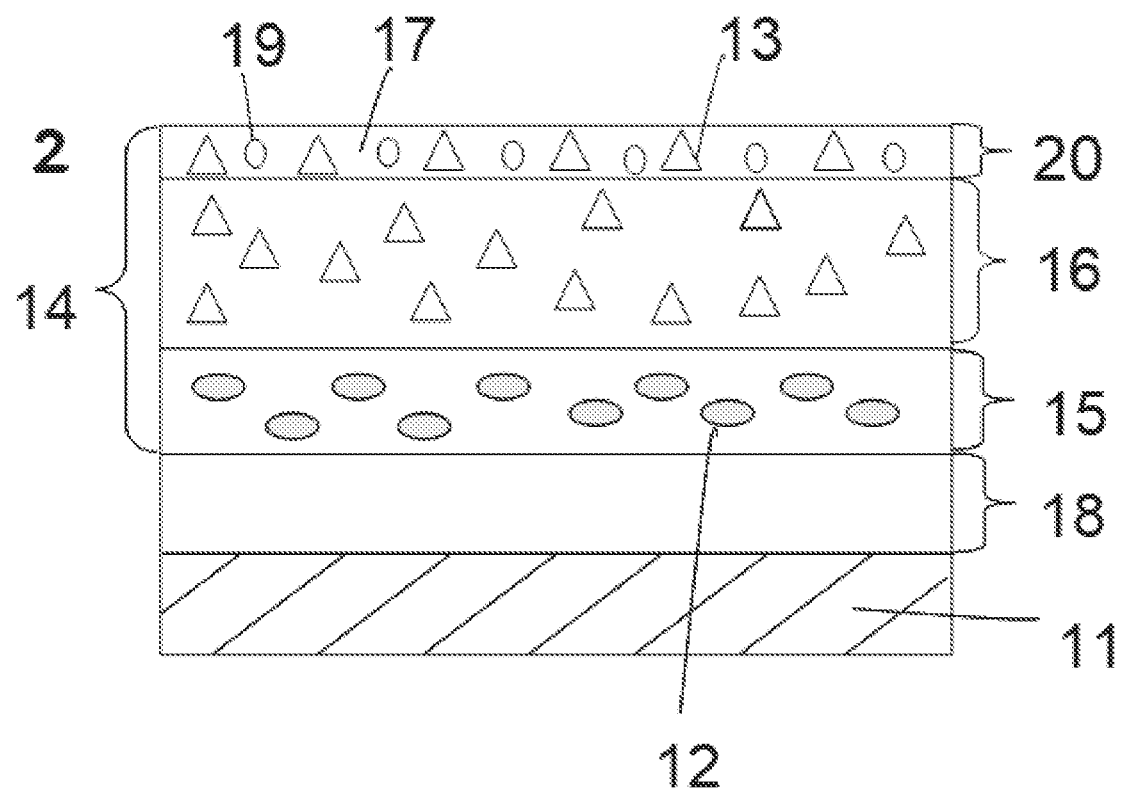
FIG. 2 is a schematic cross-sectional view illustrating a configuration of a main part of a photoreceptor 2 according to the present disclosure.
Figure 3:
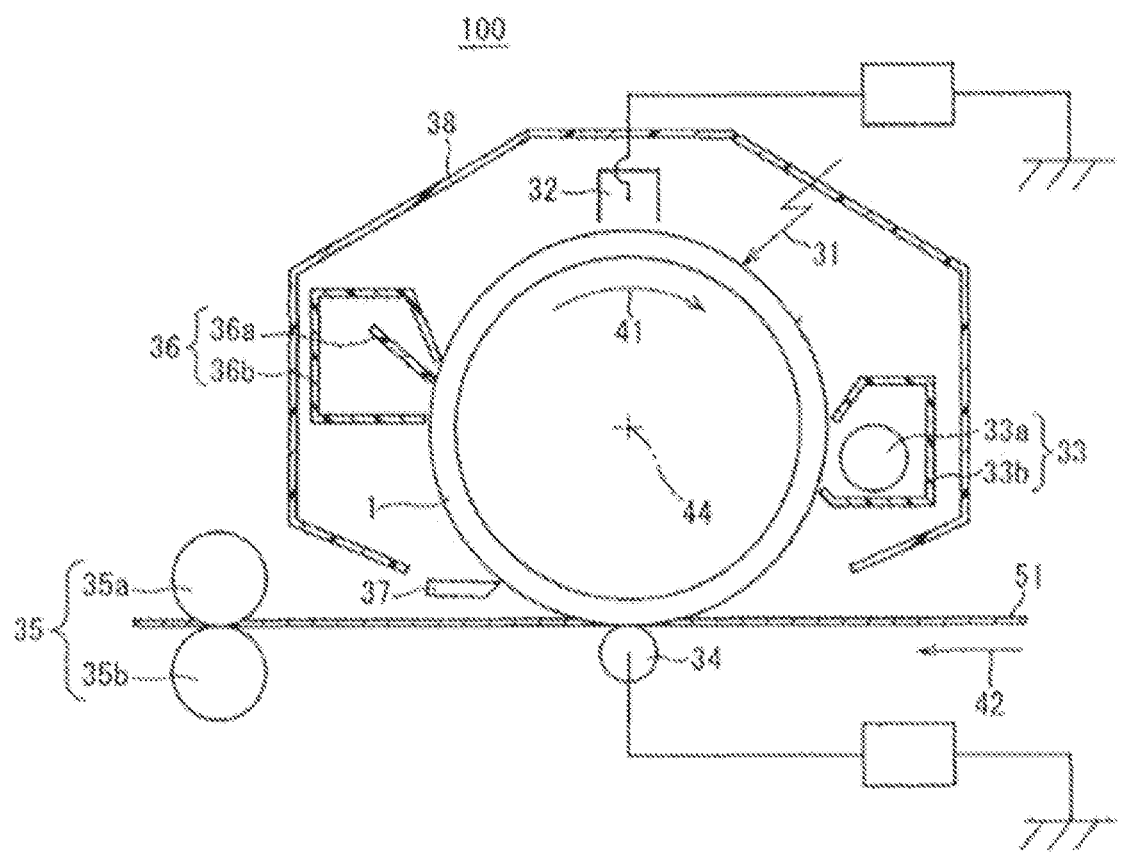
FIG. 3 is a schematic side view illustrating a configuration of a main part of an image-forming apparatus according to the present disclosure.
Figure 4:
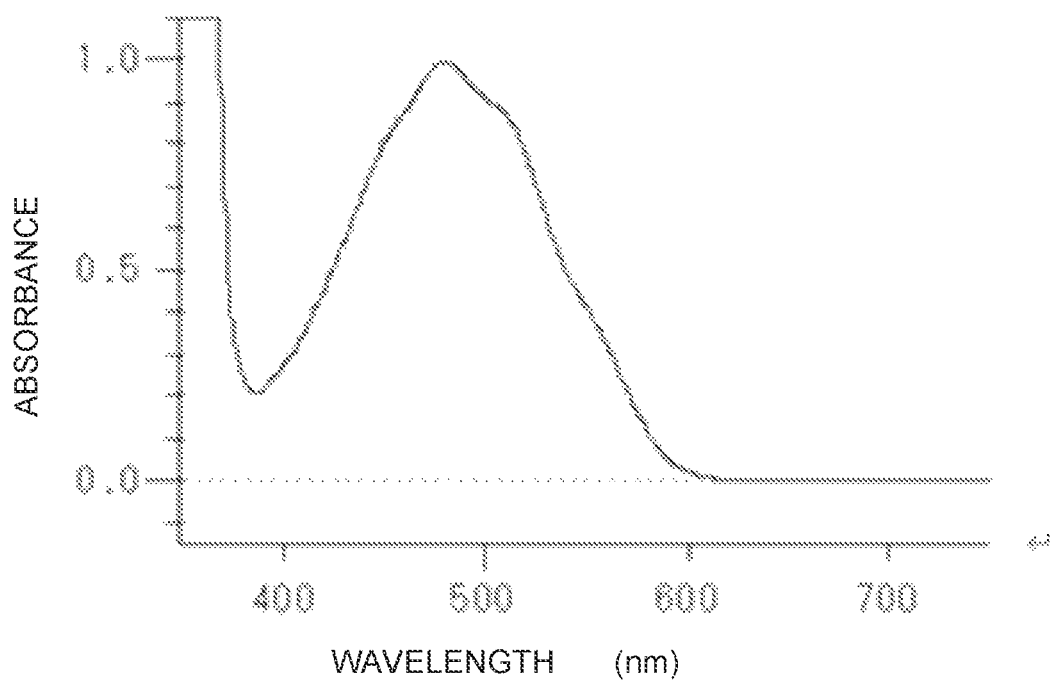
FIG. 4 is a graph presenting an absorption spectrum of a perimidine compound represented by general formula (I) according to the present disclosure.

FIG. 2 is a schematic cross-sectional view illustrating a configuration of a main part of a photoreceptor 2 according to the present disclosure. This photoreceptor 2 is a laminated photoreceptor having a protective layer 20 containing the perimidine compound 19 according to the present disclosure on the outside of the photoreceptor 1 (photoreceptive side) in FIG. 1. In the photoreceptor 2, the charge transporting layer 16 does not contain the perimidine compound 19 according to the present disclosure, but in the photoreceptor according to the present disclosure, both or either one of the charge transporting layer 16 and the protective layer 20 may contain the perimidine compound 19 according to the present disclosure.

Each constituent will be explained below.

Conductive Base 11

The conductive base has a function as an electrode of a photoreceptor and a function as a supporting member. Constituent materials of the conductive base are not particularly limited as long as the materials are used in the art. Specifically, examples of the constituent materials may include metallic materials such as aluminum, aluminum alloy, copper, zinc, stainless steel, and titanium; and polymer materials such as polyethylene terephthalate, nylon, and polystyrene that have a surface treated with metallic foil lamination, metallic vapor deposition, or vapor deposition or coating of a layer of a conductive compound such as a conductive polymer, tin oxide, and indium oxide; hard paper; and glass. Among these materials, aluminum is preferable from the viewpoint of ease of processing, and aluminum alloys such as JIS3003 series, JIS5000 series, and JIS6000 series are particularly preferable.

A shape of the conductive base is not limited to the cylindrical shape (drum shape) as illustrated in FIG. 5, and may be a sheet shape, a columnar shape, an endless belt shape, or the like.

In addition, as necessary, a surface of the conductive base may be treated with anodic oxidation coating, surface treatment with chemicals or hot water, coloring, or irregular reflection treatment such as surface roughening without affecting an image quality, for the purpose of preventing interference fringes due to laser beam.

Undercoat Layer (Also Referred to as "Intermediate Layer") 18

The photoreceptor according to the present disclosure preferably includes the undercoat layer 18 disposed between the conductive base 11 and the photoreceptive layer 14.

The undercoat layer generally coats irregularity on the surface of the conductive base to even out the irregularity to increase film formability of the photoreceptive layer i.e., in this specification, the charge generating layer, and suppresses peeling-off of the photoreceptive layer from the conductive base to improve adhesiveness between the conductive base and the photoreceptive layer. Specifically, it is possible to prevent injection of charges from the conductive base to the photoreceptive layer, to prevent reduction of chargeability of the photoreceptive layer, and to prevent image fogging (so-called a black spot).

The undercoat layer can be formed by, for example, dissolving a binder resin in an appropriate solvent to prepare an undercoat layer coating liquid, applying the coating liquid on the surface of the conductive base, and removing the organic solvent by drying.

Examples of the binder resin may include, in addition to a binder resin similar to that included in the photoreceptive layer described later, naturally-occurring polymer materials such as casein, gelatin, polyvinyl alcohol, and ethyl cellulose. Each of these binder resins may be used alone or in combination of two or more types.

The binder resin is required to have characteristics such as not to develop dissolution in or swelling to a solvent used in forming the photoreceptor layer on the undercoat layer, to have excellent adhesiveness to the conductive base, and to have flexibility. Accordingly, among the binder resins described above, a polyamide resin is preferable, and an alcohol-soluble nylon resin is particularly preferable.

Examples of the alcohol-soluble nylon resin may include a homopolymerized or copolymerized nylon such as 6-nylon, 66-nylon, 610-nylon, 11-nylon, and 12-nylon; and a chemically-modified nylon resin such as N-alkoxy methyl-modified nylon.

Examples of the solvents for dissolving or dispersing the resin materials may include water; alcohols such as methanol, ethanol, and butanol; glymes such as methyl carbitol and butyl carbitol; chlorine-based solvents such as dichloroethane, chloroform, and trichloroethane; acetone; dioxolane; and mixture solvents derived by mixing two or more types of these solvents. Among these solvents, non-halogen organic solvents are suitably used out of consideration for the global environment.

Also, the undercoat layer coating liquid may contain a metal oxide particle.

The metal oxide particle can easily modulate a volume resistance value of the undercoat layer, further suppress injection of charges to the photoreceptive layer, as well as maintain the electric properties of the photoreceptor under a variety of environments.

Examples of the metal oxide particle may include titanium oxide, aluminum oxide, aluminum hydroxide, and tin oxide.

A ratio (C/D) of a total mass C of the binder resin and the metal oxide particle to a mass D of the solvent in the undercoat layer coating liquid is preferably 1/99 to 40/60, particularly preferably 2/98 to 30/70.

In addition, a ratio E/F of a mass E of the binder resin to a mass F of the metal oxide particle is preferably 90/10 to 1/99, particularly preferably 70/30 to 5/95.

For the purpose of dispersing the metal oxide particle in the undercoat layer coating liquid, a known apparatus may be used, such as a ball mill, a sand mill, an attritor, a vibration mill, a sonic disperser, and a paint shaker.

As a method for applying the undercoat layer coating liquid, it is only necessary to appropriately select an optimum method in consideration of physical properties and productivity of the coating liquid, and examples of the method may include a spray method, a bar coating method, a roll coating method, a blade method, a ring method, and an immersion coating method. Among these methods, in the immersion coating method, a substrate is immersed in a coating bath filled with a coating liquid, and then raised at a constant speed or a continuously changing speed to form a layer on the surface of the substrate. This immersion coating method is relatively simple and excellent in the productivity and the cost, and therefore can be suitably used for manufacturing the photoreceptor. An apparatus used in the immersion coating method may be equipped with a coat liquid disperser typified by an ultrasonic wave generator for the purpose of stabilizing dispersibility of the coating liquid.

The solvent in the coating film may be removed by natural drying, but may be forcibly removed by heating.

A temperature in such a drying step is not particularly limited as long as the solvent used can be removed, but the temperature is preferably about 50 to 140°C., and particularly preferably about 80 to 130° C. If the drying temperature is lower than 50° C., the drying time may be prolonged, and the solvent does not sufficiently evaporate and remains in the photoreceptor layer in some cases. In addition, if the drying temperature is higher than about 140° C., the electric properties of the photoreceptor during repeated use becomes poor and an obtained image may deteriorate.

Such a temperature condition is common in formation of not only the undercoat layer but also a layer such as a photoreceptive layer described later, and other treatments.

A film thickness of the undercoat layer is not particularly limited, but is preferably 0.01 to 20 μm, more preferably 0.05 to 10 μm.

If the film thickness of the undercoat layer is smaller than 0.01 μm, the layer may not substantially function as an undercoat layer, fail to coat a defect on the conductive base to provide an even surface property, and fail to prevent injection of charges from the conductive base to the photoreceptive layer. On the other hand, if the film thickness of the undercoat layer is larger than 20 μm, an even undercoat layer may be less likely to form, and sensitivity of the photoreceptor may also be reduced.

Additionally, when a constituent material of the conductive base is aluminum, a layer containing alumite (alumite layer) can be formed to be used as the undercoat layer.

Charge Generating Layer 15

The charge generating layer has a function of generating charges by absorbing an emitted light such as a semiconductor laser beam in an image-forming apparatus or the like. The charge generating layer contains a charge generating substance as a main component and, as necessary, contains a binder resin and additives.

As the charge generating substance, a compound used in the art can be used, and specific examples thereof may include azo-based pigments such as monoazo-based pigments, bisazo-based pigments, and trisazo-based pigments; indigo-based pigments such as indigo and thioindigo; perylene-based pigments such as perylene imide and perylene anhydride; polycyclic quinone-based pigments such as anthraquinone and pyrene quinone: phthalocyanine-based pigments such as metallic phthalocyanines including titanyl phthalocyanine and metal-free phthalocyanines; organic photoconductive materials such as squarylium dyes, pyrylium salts, thiopyrylium salts, and triphenylmethane-based pigments; and inorganic photoconductive materials such as selenium and amorphous silicon, from which one having sensitivity in an exposure wavelength range can be appropriately selected to be used. Each of these charge generating substances may be used alone or in combination of two or more types. Among these charge generating substances, a titanyl phthalocyanine represented by the following general formula (A) is preferably used:

[Formula 3]

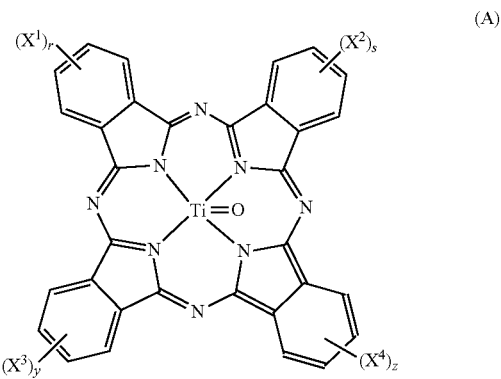

(A)

(wherein $X^1$, $X^2$, $X^3$, and $X^4$ are identically or independently a halogen atom, an alkyl group, or an alkoxy group, and r, s, y, and z are identically or independently an integer of 0 to 4).

The titanyl phthalocyanine is a charge generating substance that has a high charge generating efficiency and charge injection efficiency in an emission wavelength range (near-infrared light) of laser beam and LED light currently and commonly used, and can generate a large amount of charges by absorbing light, as well as efficiently inject the generated charges into a charge transporting substance 13 without accumulating the charges thereinside.

The titanyl phthalocyanine represented by general formula (A) can be manufactured e.g. by a known manufacture method such as a method described in Moser, Frank H and Arthur L. Thomas, "Phthalocyanine Compounds", Reinhold Publishing Corporation, New York, 1963.

For example, among titanyl phthalocyanine compounds represented by general formula (A), an unsubstituted titanyl phthalocyanine in which r, s, y, and z are 0 can be obtained by heat-melting phthalonitrile and titanium tetrachloride or heat-reacting them in a suitable solvent such as α-chloronaphthalene to synthesize a dichlorotitanyl phthalocyanine, and then hydrolyzing the dichlorotitanyl phthalocyanine with a base or water. In addition, the titanyl phthalocyanine composition can also be manufactured by heat reaction of isoindoline with titanium tetraalkoxide such as tetrabutoxytitanium in a suitable solvent such as N-methylpyrrolidone.

Examples of the method for forming the charge generating layer may include a method of vacuum-depositing the charge generating substance on the conductive base, and a method of applying a charge generating layer coating liquid obtained by dispersing the charge generating substance into a solvent, on the conductive base. Among these methods, it is preferable to use a method of dispersing the charge generating substance in a binder resin solution obtained by mixing the binder resin into a solvent in accordance with a conventional known method, and applying the charge generating layer coating liquid on the conductive base. This method will be explained below.

The binder resin is not particularly limited and can employ any resin known in the art, and examples of the binder resin may include resins such as polyester, polystyrene, polyurethane, phenol resins, alkyd resins, melamine resins, epoxy resins, silicone resins, acrylic resins, methacrylic resins, polycarbonate, polyarylate, polyphenoxy, polyvinyl butyral, and polyvinyl formal, as well as copolymer resins containing two or more of repeated units constituting these resins.

Examples of the copolymer resins may include insulative resins such as vinyl chloride-vinyl acetate copolymer resins, vinyl chloride-vinyl acetate-maleic anhydride copolymer resins, and acrylonitrile-styrene copolymer resins. Each of these resins may be used alone or in combination of two or more types.

Examples of the solvent may include halogenated hydrocarbons such as dichloromethane and dichloroethane; ketones such as acetone, methylethylketone, and cyclohexanone; esters such as ethyl acetate and butyl acetate; ethers such as tetrahydrofuran (THF) and dioxane; alkyl ethers of ethylene glycol such as 1,2-dimethoxy ethane; aromatic hydrocarbons such as benzene, toluene, and xylene, and polar aprotic solvents such as N,N-dimethylformamide and N,N-dimethylacetamide. Each of these solvents may be used alone or in combination of two or more types.

As for a blending ratio of the charge generating substance and the binder resin, the ratio of the charge generating substance is preferably in a range of 10 to 99% by mass.

If the ratio of the charge generating substance is lower than 10% by mass, sensitivity may decrease. On the other hand, if the ratio of the charge generating substance is higher than 99% by mass, not only the film strength of the charge generating layer may decrease, but also dispersibility of the charge generating substance may reduce to increase large rough particles, thus reducing surface charges of an area other than a part to be deleted by exposure and generating many image defects, especially image fogs, so-called black spots, where toner adheres to a white ground and forms minute black dots.

Before dispersing the charge generating substance into a binder resin solution, the charge generating substance may be grinded with a grinder in advance. Examples of the grinders used for the grinding may include a ball mill, a sand mill, an attritor, a vibration mill, and a sonic disperser.

Examples of a disperser used in dispersing the charge generating substance into the binder resin solution may include a paint shaker, a ball mill, and a sand mill. As conditions for this dispersion, it is only necessary to select appropriate conditions for preventing contamination with impurities due to wear or the like of members constituting the container and disperser to be used.

Examples of the method for applying the charge generating layer coating liquid include the same methods as for applying the undercoat layer coating liquid, and the immersion coating method is particularly preferable.

A film thickness of the charge generating layer is not particularly limited, but is preferably 0.05 to 5 μm, more preferably 0.1 to 1 μm, If the film thickness of the charge generating layer is smaller than 0.05 μm, a light absorption efficiency may decrease to lower the sensitivity of the photoreceptor. On the other hand, if the film thickness of the charge generating layer is larger than 5 μm, the charge transfer inside the charge generating layer is at a rate-limiting stage in a process of erasing the charges on the photoreceptive layer surface, and the sensitivity of the photoreceptor may decrease.

Charge Transporting Layer 16

The charge transporting layer has a function of receiving charges generated in the charge generating substance and transporting the charges to the photoreceptor surface, and contains the charge transporting substance, a filler, and a binder resin, and as necessary, the perimidine compound according to the present disclosure, and other additives.

The perimidine compound according to the present disclosure is represented by general formula (I):

[Formula 4]

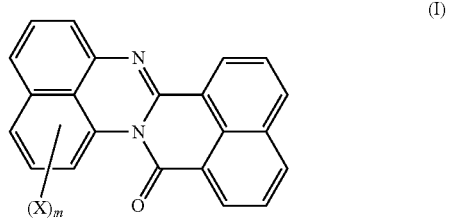

(I)

(wherein X represents hydrogen atom, an alkyl group having 1 to 6 carbon atoms, or an alkoxy group having 1 to 6 carbon atoms, and m represents an integer of 1 to 6).

Examples of the alkyl group having 1 to 6 carbon atoms may include methyl, ethyl, n-propyl, isopropyl, n-butyl, isobutyl, sec-butyl, tert-butyl, n-pentyl, and n-hexyl.

Examples of the alkoxy group having 1 to 6 carbon atoms may include methoxy, ethoxy, n-propoxy, isopropoxy, tert-butoxy, n-pentyloxy, and n-hexyloxy.

Above all, a perimidine compound (C.I. Solvent Red 179) in which the substituent X is hydrogen atom and the exponent m is 6 in general formula (I) is particularly preferable in terms of excellent effects of the present disclosure, availability of materials, and the like.

The perimidine compound according to the present disclosure can be synthesized by methods described in Examples 1 and 4 of JP 2001-501667 W. Commercial products, e.g. Amesolve Red A manufactured by American Dyestuff Corporation, KP Plast Red H2G manufactured by MINYA Chemical Industry Co., Ltd., and Red E2G manufactured by TOYO SCIENCE CO., LTD can be used in the present disclosure.

As the charge transporting substance, a compound used in the art can be used.

Specific examples of the charge transporting substance include carbazole derivatives, pyrene derivatives, oxazole derivatives, oxadiazole derivatives, thiazole derivatives, thiadiazole derivatives, triazole derivatives, imidazole derivatives, imidazolone derivatives, imidazolidine derivatives, bis(imidazolidine) derivatives, styryl compounds, hydrazone compounds, polycyclic aromatic compounds, indole derivatives, pyrazoline derivatives, oxazolone derivatives, benzimidazole derivatives, quinazoline derivatives, benzofuran derivatives, acridine derivatives, phenazine derivatives, aminostilbene derivatives, triarylamine derivatives, triarylmethane derivatives, phenylenediamine derivatives, stilbene derivatives, butadiene derivatives, enamine derivatives, benzidine derivatives, polymers having a group derived from these compounds in a main chain or a side chain (such as poly-N-vinyl carbazole, poly-1-vinyl pyrene, ethylcarbazole-formaldehyde resin, triphenyl methane polymer, and poly-9-vinyl anthracene), and polysilane. Each of these charge transporting substances may be used alone or in combination of two or more types.

Among these various charge transporting substances, in terms of electrical properties, durability, and chemical stability, stilbene derivatives, butadiene derivatives, enamine derivatives, and conjugates of several types of these compounds are preferable. Above all, stilbene derivatives are more preferable, and stilbene compounds represented by the following general formula (II) is particularly preferable:

[Formula 5]

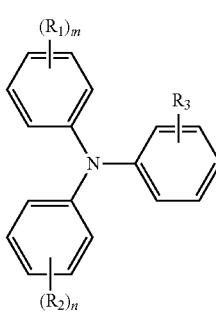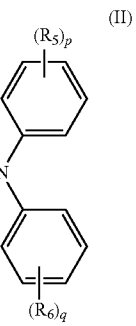

(II)

(wherein $R_1$, $R_2$, $R_5$, and $R_6$ are identically or independently an alkyl group, an alkoxy group, an aryl group, an aralkyl group, or a halogen group; m, n, p, and q are identically or independently an integer of 0 to 3; and $R_3$ and $R_4$ are identically or independently hydrogen atom or an alkyl group).

The substituents R1, R2, R5, and R6 in general formula (II) will be explained.

Examples of the alkyl groups may include alkyl groups having to 6 carbon atoms, such as methyl, ethyl, n-propyl, isopropyl, n-butyl, isobutyl, sec-butyl, tert-butyl, n-pentyl, and n-hexyl.

Examples of the alkoxy groups may include alkoxy groups having 1 to 6 carbon atoms such as methoxy, ethoxy, n-propoxy, isopropoxy, tert-butoxy, n-pentyloxy, and n-hexyloxy.

Examples of the aryl groups may include phenyl, naphthyl, anthryl, phenanthryl, fluorenyl, biphenylyl, and o-terphenyl.

Examples of the aralkyl groups may include benzyl, phenethyl, benzhydryl, and trityl.

Examples of the halogen atom may include fluorine, chlorine, bromine, and iodine.

The m, n, p, and q, which represent exponents of the substituents $R_1$, $R_2$, $R_5$ and $R_6$, are identically or independently an integer of 0 to 3. If the exponent is 2 or larger, each of the substituents may be different from each other.

In addition, examples of the alkyl groups on the substituents $R_3$ and $R_4$ in general formula an may include alkyl groups having 1 to 3 carbon atoms, such as methyl, ethyl, n-propyl, and isopropyl.

The stilbene compound represented by the general formula (II) can be synthesized by e.g. a method described in Japanese Patent No. 3272257.

Examples of the stilbene compound represented by general formula (II) may include the following compounds (1) to (3), and in view of electric properties and solubility, the compound (1) is particularly preferable.

[Formula 6]

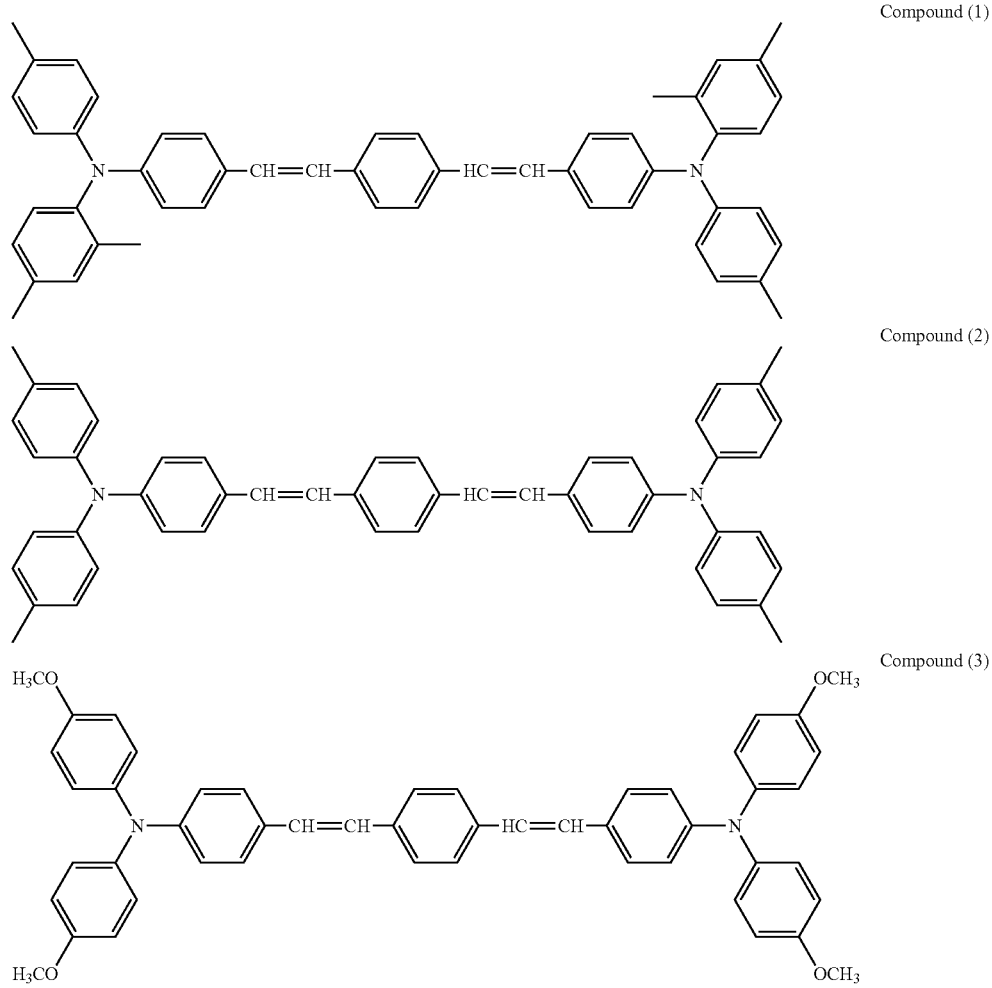

Compound (1)

Compound (2)

Compound (3)

A method of forming the charge transporting layer is preferably a method in which the charge transporting substance and the perimidine compound according to the present disclosure are added to a binder resin solution obtained by mixing a binder resin into a solvent and dispersed according to a conventional known method to prepare a charge transporting layer coating liquid, and the charge transporting layer coating liquid is applied on the charge generating layer. This method will be explained below.

The binder resin is not particularly limited, and any resin known in the art can be used as the binder resin. Examples of the binder resin may include vinyl polymer resins such as polymethylmethacrylate, polystyrene, and polyvinyl chloride, and copolymer resins thereof; resins such as polycarbonate, polyester, polyester carbonate, polysulfone, polyphenoxy, epoxy resins, silicone resins, polyarylate, polyphenylene one oxide, polyamide, polyether, polyurethane, polyacrylamide, and phenol resins; and thermosetting resins obtained by partially crosslinking these resins. Each of these binder resins may be used alone or in combination of two or more types.

Above all, polycarbonate resins and polyarylate resins are particularly preferable because they are excellent in compatibility with the charge transporting substance, also in electric insulation, transparency, electric properties, film performance, wear resistance, and the like.

A ratio A/B of the charge transporting substance (A) to the binder resin (B) is preferably 10/12 to 10/30.

If the ratio of the binder resin is increased with a ratio A/B of lower than 10/30, viscosity of the coating liquid is increased when forming the charge transporting layer by the immersion coating method, and therefore an application speed decreases and the productivity greatly worsens. Moreover, when the content of the solvent in the coating liquid is increased for preventing increase in viscosity of the coating liquid, a brushing phenomenon may occur to generate white turbidity in the charge transporting layer thus formed. On the other hand, if the ratio of the binder resin is decreased with a ratio A/B of higher than 10/12, printing durability may be more reduced relative to the case with a high ratio of the binder resin, thus increasing the amount of wear of the photoreceptive layer.

Preferably, a content of the perimidine compound is 0.05 to 1.5% by mass based on the total solid content of the charge transporting layer. If the content of the perimidine compound is less than 0.05% by mass, an effect on light resistance may not be sufficiently provided. On the other hand, if the content of the perimidine compound is more than 1.5% by mass, the electrical properties may deteriorate. The content of the perimidine compound is more preferably 0.15 to 0.80% by mass.

For the purpose of improving film formability; flexibility, and surface smoothness, the charge transporting layer may contain additives such as plasticizers and leveling agents, as necessary.

Examples of the plasticizer may include dibasic acid esters such as phthalic acid esters, fatty acid esters, phosphoric acid esters, chlorinated paraffins, and epoxy-type plasticizers.

Examples of the leveling agents may include silicone-based leveling agents. For the purpose of enhancing the mechanical strength and improving the electrical properties, the charge transporting layer may also contain microparticles of an inorganic compound or an organic compound.

Examples of the solvents may include aromatic hydrocarbons such as benzene, toluene, xylene, and monochlorobenzene; halogenated hydrocarbons such as dichloromethane and dichloroethane; ethers such as THF, dioxane, and dimethoxy methyl ether; and polar aprotic solvents such as N,N-dimethylformamide. Additionally, a solvent such as alcohols, acetonitrile, and methylethylketone can also be further added to be used, as necessary. Among these solvents, non-halogen organic solvents are suitably used out of consideration for the global environment. Each of these solvents may be used alone or in combination of two or more types.

For example, in the same manner as for forming the charge generating layer 15 described above, the charge transporting layer is formed by dissolving or dispersing the charge transporting substance 13 and the binder resin 17, and if required, the above-mentioned additives into an appropriate solvent to prepare a charge transporting layer coating liquid, and applying the charge transporting layer coating liquid on the charge generating layer 15 by spraying, bar coating, roll coating, a blade technique, a ring technique, immersion application, or the like. Among these application methods, immersion application is particularly excellent in view of various points as described above, and thus also often utilized in forming the charge transporting layer.

Preferably the charge transporting layer has a film thickness of 18 to 42 μm.

If the film thickness of the charge transporting layer is smaller than 18 μm, the effect on light resistance may not be sufficient. On the other hand, if the film thickness of the charge transporting layer is larger than 42 μm, the electric properties may deteriorate. The film thickness of the charge transporting layer is more preferably 25 to 37 μm.

Protective Layer

The photoreceptor according to the present disclosure may have a protective layer on the photoreceptive layer, as illustrated in FIG. 2.

The protective layer has a function of improving durability of the photoreceptor, and contains the binder resin and, as necessary, the perimidine compound according to the present disclosure, and other additives. For the purpose of stabilizing the electric properties, the protective layer may also contain one type or two or more types of the same charge transporting substances as in the charge transporting layer.

As the binder resin, a bindable resin used in the art can be used. Examples of the binder resin include resins such as polystyrene, polyacetal, polyethylene, polycarbonate, polyarylate, polysulfone, polypropylene, and polyvinyl chloride. Each of these binder resins may be used alone or in combination of two or more types.

Above all, in view of wear properties and electric properties, polycarbonate and polyarylate are particularly preferable.

The protective layer may also include a filler material added for the purpose of improving wear resistance.

Examples of an organic filler material may include a fluororesin powder such as polytetrafluoroethylene, a silicone resin powder, an a-carbon powder. Examples of an inorganic filler material may include inorganic materials such as: a metal powder such as copper, tin, aluminum, and indium; a metal oxide such as silica, tin oxide, zinc oxide, titanium oxide, indium oxide, antimony oxide, bismuth oxide, antimony-doped tin oxide, and tin-doped indium oxide; and potassium titanate. In terms of filler hardness, the inorganic filler material is particularly preferable.

An average primary particle diameter of the filler is preferably 0.01 to 0.5 μm in terms of light transmittance and wear resistance of the protective layer.

In terms of improving dispersibility in the coating liquid for coating formation, or the like, the surface of the filler material may be treated with inorganic or organic materials. For example, as a water-repellent treatment, the surface of the filler material may be treated with a silane coupling agent, a fluorine-based silane coupling agent, a higher fatty acid, alumina, zirconia, tin oxide, or silica.

The higher the ratio of the filler material in the protective layer is, the better the wear resistance is, but the high ratio of the filler material may cause adverse effects such as deterioration of the electric properties and decrease in a writing light transmittance of the protective layer. Thus, the filler material is generally 50% by mass or less, preferably 30% by mass or less based on the total solid content.

The content of the perimidine compound is preferably 0.3 to 7% by mass based on the total solid content of the protective layer.

If the content of the perimidine compound is less than 0.3% by mass, an effect on light resistance may not be sufficiently provided. On the other hand, if the content of the perimidine compound is more than 7% by mass, the electrical properties may deteriorate. The content of the perimidine compound is more preferably 1 to 4% by mass.

Preferably, the protective layer has a film thickness of 3 to 7 μm If the film thickness of the protective layer is smaller than 3 μm, the effects on durability and light resistance may not be sufficient. On the other hand, if the film thickness of the protective layer is larger than 7 μm, the electric properties may deteriorate. The film thickness of the protective layer is more preferably 4 to 6 μm.

(2) Image-Forming Apparatus 100

The image-forming apparatus according to the present disclosure characteristically includes at least the photoreceptor according to the present disclosure, an electrifier for electrifying the photoreceptor, an exposer for exposing the electrified photoreceptor to form an electrostatic latent image, a developer for developing the electrostatic latent image formed by the exposure to form (visualize) a toner image, a transferee for transferring the toner image formed by the development onto a recording medium, a fuser for fusing the transferred toner image onto the recording medium to form an image, a cleaner for removing and recovering the toner remaining on the photoreceptor, and a charge eliminator for eliminating surface charges remaining on the photoreceptor.

The image-forming apparatus according to the present disclosure and operation thereof will be explained with reference to the figures, but are not limited to the following description.

FIG. 2 is a schematic side view illustrating a configuration of the image-forming apparatus according to the present disclosure.

The image-forming apparatus (laser printer) 100 in FIG. 2 is composed of the photoreceptor 1 according to the present disclosure, an exposer (semiconductor laser) 31, an electrifier (electrifying device) 32, a developer (developing device) 33, a transferer (transfer electrifying device) 34, a conveyor belt (not illustrated), a fuser (fusing device) 35, and a cleaner (cleaning device) 36. Reference numeral 51 represents a recording medium (recording paper or transfer paper).

The photoreceptor 1 is rotatably supported by the main body of the image-forming apparatus 100, and rotationally driven around a rotation axis 44 in a direction of an arrow 41 by a driver not illustrated. The driver is composed of e.g. an electric motor and a reduction gear and transmits the driving force to the conductive base constituting a core body of the photoreceptor 1, so that the photoreceptor 1 is rotationally driven at a predetermined peripheral velocity. The electrifier (electrifying device) 32, the exposer 31, the developer (developing device) 33, the transferer (transfer electrifying device) 34, and the cleaner (cleaning device) 36 are arranged in this order along the outer peripheral face of the photoreceptor 1 from an upstream side to a downstream side in the rotation direction of the photoreceptor 1 indicated by the arrow 41.

The electrifying device 32 is an electrifier that uniformly electrifies the outer peripheral face of the photoreceptor 1 at a predetermined potential. The exposer 31 includes a semiconductor laser as a light resource, and emits laser beam light output from the light source, onto the surface of photoreceptor 1 between the electrifying device 32 and the developing device 33, thereby applying exposure corresponding to image information, onto the outer peripheral face of the photoreceptor 1 electrified. The lights are repeatedly scanned in an extending direction of the rotation axis 44 of the photoreceptor 1 as a main scanning direction, and these lights form an image, so that electrostatic latent images are sequentially formed on the surface of the photoreceptor 1. That means, the presence or absence of laser beam irradiation causes differences in the electrification amount of the photoreceptor 1 uniformly electrified by the electrifying device 32, to form the electrostatic latent image.

The developing device 33 is a developer that develops, using a developing powder (toner), the electrostatic latent image formed on the surface of the photoreceptor 1 by exposure and is arranged facing the photoreceptor 1, and includes a developing roller 33*a* for feeing the toner to the outer peripheral face of the photoreceptor 1, and a casing 33*b* for supporting the developing roller 33*a* rotatably around a rotation axis parallel to the rotation axis 44 of the photoreceptor 1 and accommodating the developing powder containing the toner in its own internal space.

The transfer electrifying device 34 is a transferer for transferring a toner image as a visible image formed on the outer peripheral face of the photoreceptor 1 by development onto a transfer paper 51 that is a recording medium fed to between the photoreceptor 1 and the transfer electrifying device 34 from an arrow 42 direction by means of a conveyor not illustrated. The transfer electrifying device 34 is e.g. a contact-type transferer that includes the electrifies and transfers a toner image onto the transfer paper 51 by applying charges antipolar to the toner onto the transfer paper 51.

The cleaner 36 is a cleaner for removing and recovering the toner remaining on the outer peripheral face of the photoreceptor 1 after the transfer operation using the transfer electrifying device 34, and includes a cleaning blade 36*a* for peeling off the toner remaining on the outer peripheral face of the photoreceptor 1, and a recovery casing 36*b* for accommodating the toner peeled off by the cleaning blade 36*a*. In addition, the cleaner 36 is disposed together with a charge eliminating lamp not illustrated.

In addition, the image-forming apparatus 100 has the fusing device 35 as a fuser for fusing the transferred image, on the downstream side where the transfer paper 51 that has passed between the photoreceptor 1 and the transfer electrifying device 34 is conveyed. The fusing device 35 includes a heat roller 35*a* having a heater not illustrated, and a pressure roller 35*b* arranged opposite to the heat roller 35*a* and pressed by the heat roller 35*a* to form a contact portion.

The reference numeral 37 indicates a separator that separates the transfer paper from the photoreceptor, and the reference numeral 38 indicates a casing that accommodates each of the aforementioned sections in the image-forming apparatus.

The image forming operation by the image-forming apparatus 100 is performed as follows.

First, once the photoreceptor 1 is rotationally driven in the direction of the arrow 41 by the driver, the surface of the photoreceptor 1 is uniformly electrified at a predetermined positive potential by the electrifying device 32 provided on the upstream side in the rotational direction of the photoreceptor 1 relative to an image-forming point of lights from the exposer 31.

Subsequently, the exposer 31 emits light according to the image information toward the surface of the photoreceptor 1. In the photoreceptor 1, the surface charges of the part irradiated with light are removed by this exposure, and a difference is caused between the surface potential of the part irradiated with light and the surface potential of the part not irradiated with light, so that an electrostatic latent image is formed.

From the developing device 33 disposed on the downstream side in the rotational direction of the photoreceptor 1 relative to the image-forming point of the lights from the exposer 31, the toner is fed to the surface of the photoreceptor 1 on which an electrostatic latent image is formed, and then the electrostatic latent image is developed to form a toner image.

The transfer paper 51 is fed to between the photoreceptor 1 and the transfer electrifying device 34 in synchronization with the exposure to the photoreceptor 1. Charges antipolar to the toner are applied to the fed transfer paper 51 by the transfer electrifying device 34, so that the toner image formed on the surface of the photoreceptor 1 is transferred onto the transfer paper 51.

The transfer paper 51 to which the toner image is transferred is conveyed to the fusing device 35 by the conveyor, and heated and pressurized while passing through the contact portion between the heat roller 35*a* and the pressure roller 35*b* of the fusing device 35, and the toner image is fused to the transfer paper 51 to obtain a robust image. The transfer paper 51 on which the image is formed in this way is discharged to the outside of the image-forming apparatus 100 by the conveyor.

On the other hand, the toner remaining on the surface of the photoreceptor 1 even after the transfer of the toner image by the transfer electrifying device 34 is peeled off and recovered from the surface of the photoreceptor 1 by the cleaner 36. The charges on the surface of the photoreceptor 1 from which the toner has been removed in this way are removed by the light from the charge eliminating lamp, and the electrostatic latent image on the surface of the photoreceptor 1 disappears. After that, the photoreceptor 1 is further rotationally driven, and a series of operations starting from electrification are repeated again to continuously form the images,

(3) Process Cartridge

The process cartridge according to the present disclosure characteristically includes the photoreceptor according to the present disclosure, and at least one selected from the electrifier for electrifying the photoreceptor, the developer for developing an electrostatic latent image formed by exposure to form a toner image, and the cleaner for removing the toner remaining on the photoreceptor.

For example, the process cartridge according to the present disclosure is composed of the photoreceptor according to the present disclosure, an electrifying device, a developing device, and a cleaning device, which are integrated on the supporting member. Incorporation of such a process cartridge into the image-forming apparatus 100 means that the image-forming apparatus 100 includes each part as a constituent of the process cartridge.

Since the process cartridge is attachable to and detachable from the image-forming apparatus 100, exchange of the process cartridge due to consumption is facilitated.

EXAMPLES

Hereinafter, the present disclosure will be specifically explained in Examples and Comparative Examples with reference to the figures, but these examples do not limit the present disclosure.

Example 1

To 25 parts by mass of methyl alcohol, 3 parts by mass of titanium oxide (trade name: TIPAQUE TTO-D-1, manufactured by ISHIHARA SANGYO KAISHA, LTD.) and 2 parts by mass of copolymerized polyamide (nylon) (trade name: Amilan (registered trademark), grade: CM8000, manufactured by Toray Industries, Inc.) were added, which was dispersed in a paint shaker for 8 hours to prepare 3 litters of an undercoat layer coating liquid.

The undercoat layer coating liquid thus obtained was filled in a coating layer, into which an aluminum drum-shaped base having a diameter of 30 mm and a length of 255 mm as the conductive base 11 was immersed, then pulled up. The coating film thus obtained was dried naturally to form the undercoat layer 18 having a film thickness of 1 μm on the conductive base 11.

A titanyl phthalocyanine represented by the following structural formula, which was to be used as the charge generating substance, was prepared in advance.

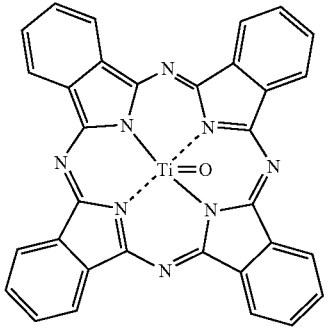

[Formula 7]

After mixing 29.2 g of diiminoisoindoline and 200 mL of sulfolane, 17.0 g of titanium tetraisopropoxide was further added, and reacted under nitrogen atmosphere at 140° C. for 2 hours. The reaction mixture thus obtained was allowed to cool, and then a precipitate was filtered off, washed serially with chloroform and 2% aqueous hydrochloric acid solution, further washed serially with water and methanol, and dried to provide 25.5 g of a blue-violet crystal.

As a result of chemical analysis of the compound thus obtained, the compound was confirmed to be the titanyl phthalocyanine represented by the above structural formula (yield: 88.5%).

To 98 parts by mass of methylethylketone, 1 part by mass of the titanyl phthalocyanine thus obtained and 1 part by mass of a butyral resin (trade name: S-LEC BM-2, manufactured by Sekisui Chemical Company, Limited) were added, and dispersed with a paint shaker for 2 hours to prepare 3 litters of charge generating layer coating liquid.

The charge generating layer coating liquid thus obtained was applied on the undercoat layer in the same immersion technique as for the formation of the undercoat layer, and the coating film thus obtained was dried naturally to form a charge generating layer having a film thickness of 0.3 μm.

Then, 250 g of compound (1) as the charge transporting substance, 375 g of polycarbonate (trade name: TS2050, manufactured by Teijin Chemicals Ltd.), and 1.15 g of compound represented by general formula (I) (trade name: Amesolye Red A, manufactured by American Dyestuff Corporation) were added to 2500 g of tetrahydrofuran, mixed, and stirred in a ball mill for 15 hours to prepare 3126 g of a charge transporting layer coating liquid.

The charge transporting layer coating liquid thus obtained was applied on the charge generating layer in the same immersion technique as for the formation of the undercoat layer, and the coating film thus obtained was dried at 120° C. for 1 hour to form a charge transporting layer having a film thickness of 36 μm, thus providing the photoreceptor illustrated in FIG. 1. A compound (1) (stilbene compound) prepared in advance in accordance with the method described in Japanese Patent No. 3272257 was used as the charge transporting substance.

Example 2

In the preparation of the charge transporting layer coating liquid, a photoreceptor was prepared in the same manner as in Example 1 except that the amount of the compound represented by general formula (I) (trade name: Amesolve Red A, manufactured by American Dyestuff Corporation) was changed from 1.15 g to 4.38 g.

Example 3

A photoreceptor was prepared in the same manner as in Example 1 except that the film thickness of the charge transporting layer was changed from 36 μm to 26 μm.

Example 4

In the preparation of the charge transporting layer coating liquid, a photoreceptor was prepared in the same manner as in Example 1 except that the amount of the compound represented by general formula (I) (trade name: Amesolve Red A, manufactured by American Dyestuff Corporation) was changed from 1.15 g to 0.31 g.

Example 5

In the preparation of the charge transporting layer coating liquid, a photoreceptor was prepared in the same manner as in Example 1 except that the amount of the compound represented by general formula (I) (trade name: Amesolve Red A, manufactured by American Dyestuff Corporation) was changed from 1.15 g to 9.50 g.

Example 6

In the preparation of the charge transporting layer coating liquid, a photoreceptor was prepared in the same manner as in Example 1 except that the amount of the compound represented by general formula (I) (trade name: Amesolve Red A, manufactured by American Dyestuff Corporation) was changed from 1.15 g to 0.25 g.

Example 7

In the preparation of the charge transporting layer coating liquid, a photoreceptor was prepared in the same manner as in Example 1 except that the amount of the compound represented by general formula (I) (trade name: Amesolve Red A, manufactured by American Dyestuff Corporation) was changed from 1.15 g to 10.1 g.

Example 8

A photoreceptor was prepared in the same manner as in Example 5 except that the film thickness of the charge transporting layer was changed from 36 μm to 18 μm.

Example 9

A photoreceptor was prepared in the same manner as in Example 4 except that the film thickness of the charge transporting layer was changed from 36 μm to 42 μm.

Example 10

A photoreceptor was prepared in the same manner as in Example 5 except that the film thickness of the charge transporting layer was changed from 36 μm to 17 μm.

Example 11

A photoreceptor was prepared in the same manner as in Example 4 except that the film thickness of the charge transporting layer was changed from 36 μm to 44 μm.

Example 12

An undercoat layer and a charge generating layer were formed in the same manner as in Example 1.

Subsequently, 250 g of compound (1) as the charge transporting substance, 375 g of polycarbonate (trade name: TS2050, manufactured by Teijin Chemicals Ltd.) were added to 2500 g of tetrahydrofuran, mixed, and stirred in a ball mill for 15 hours to prepare 3125 g of a charge transporting layer coating liquid.

The charge transporting layer coating liquid thus obtained was applied on the charge generating layer in the same immersion technique as for the formation of the undercoat layer, and the coating film thus obtained was dried at 120° C. for 1 hour to form a charge transporting layer having a film thickness of 30 μm.

Subsequently, 120 g of silica particle (trade name: AEROSIL (registered trademark) RX200, manufactured by NIPPON AEROSIL CO., LTD.), 250 g of the compound (1) as the charge transporting substance, 375 of polycarbonate (trade name: TS2050, manufactured by Teijin Chemicals Ltd.), and 9.05 g of compound (1) represented by general formula (I) (trade name: Amesolve Red A, manufactured by American Dyestuff Corporation) were added to 3500 g of tetrahydrofuran, mixed, and stirred in a ball mill for 15 hours, and subjected to 5-pass dispersion using a particle dispersing apparatus (model: M-110P, manufactured by Microfluidic ChipShop GmbH) to prepare 4041 g of a protective layer coating liquid.

The protective layer coating liquid thus obtained was applied on the charge transporting layer in a spray technique, the resulting coating film was dried at 120° C. for 1 hour to form a protective layer having a film thickness of 4.5 μm, thus providing the photoreceptor illustrated in FIG. 2.

A compound (1) (stilbene compound) prepared in advance in accordance with the method described in Japanese Patent No. 3272257 was used as the charge transporting substance.

Example 13

In the preparation of the protective layer coating liquid, a photoreceptor was prepared in the same manner as in Example 12 except that the amount of the compound represented by general formula (I) (trade name: Amesolve Red A, manufactured by American Dyestuff Corporation) was changed from 9.05 g to 29.40 g.

Example 14

A photoreceptor was prepared in the same manner as in Example 12 except that the film thickness of the protective layer was changed from 4.5 μm to 5.5 μm.

Example 15

In the preparation of the protective layer coating liquid, a photoreceptor was prepared in the same manner as in Example 12 except that the amount of the compound represented by general formula (I) (trade name: Amesolve Red A, manufactured by American Dyestuff Corporation) was changed from 9.05 g to 3.00 g.

Example 16

In the preparation of the protective layer coating liquid, a photoreceptor was prepared in the same manner as in Example 12 except that the amount of the compound represented by general formula (I) (trade name: Amesolve Red A, manufactured by American Dyestuff Corporation) was changed from 9.05 g to 3.00 g.

Example 17

In the preparation of the protective layer coating liquid, a photoreceptor was prepared in the same manner as in Example 12 except that the amount of the compound represented by general formula (I) (trade name: Amesolve Red A, manufactured by American Dyestuff Corporation) was changed from 9.05 g to 1.50 g.

Example 18

In the preparation of the protective layer coating liquid, a photoreceptor was prepared in the same manner as in Example 12 except that the amount of the compound represented by general formula (I) (trade name: Amesolve Red A, manufactured by American Dyestuff Corporation) was changed from 9.05 g to 1.15 g.

Example 19

A photoreceptor was prepared in the same manner as in Example 16 except that the film thickness of the protective layer was changed from 4.5 pm to 3.0 µm.

Example 20

A photoreceptor was prepared in the same manner as in Example 15 except that the film thickness of the protective layer was changed from 4.5 µm to 7.0 µm.

Example 21

A photoreceptor was prepared in the same manner as in Example 16 except that the film thickness of the protective layer was changed from 4.5 µm to 2.0 µm.

Example 22

A photoreceptor was prepared in the same manner as in Example 15 except that the film thickness of the protective layer was changed from 4.5 µm to 8.0 µm.

Example 23

In the preparation of the charge transporting layer coating liquid, a photoreceptor was prepared in the same manner as in Example 12 except that 1.15 g of the compound represented by general formula (I) (trade name: Amesolve Red A, manufactured by American Dyestuff Corporation) was added.

Example 24

In the preparation of the charge transporting layer coating liquid, a photoreceptor was prepared in the same manner as in Example 1 except that a TPD (triphenylarnine (timer) (trade name: D2448, manufactured by Tokyo Chemical Industry Co., Ltd.) was used instead of the compound (1) as the charge transporting substance.

Comparative Example 1

In the preparation of the charge transporting layer coating liquid, a photoreceptor was prepared in the same manner as in Example 1 except that 1.15 g of the compound represented by general formula (I) (trade name: Amesolve Red A, manufactured by American Dyestuff Corporation) was not used.

Comparative Example 2

In the preparation of the charge transporting layer coating liquid, a photoreceptor was prepared in the same manner as in Example 1 except that a benzophenone-based UV absorber (2-hydroxy-4-methoxybenzophenone, manufactured by FUJIFILM Wako Pure Chemical Corporation) was used instead of the compound represented by general formula (1) (trade name: Amesolve Red A, manufactured by American Dyestuff Corporation).

Comparative Example 3

In the preparation of the charge transporting layer coating liquid, a photoreceptor was prepared in the same manner as in Example 1 except that a compound described in Example 1 of JP 2012-103333 A (trade name: Amesolve Red H, manufactured by American Dyestuff Corporation) was used instead of the compound represented by general formula (I) (trade name: Amesolve Red A, manufactured by American Dyestuff Corporation).

Comparative Example 4

In the preparation of the charge transporting layer coating liquid, a photoreceptor was prepared in the same manner as in Example 1 except a compound described in Example 1 of JP H10-048856 A (trade name: Amesolve Yellow Y, manufactured by American Dyestuff Corporation.) was used instead of the compound represented by general formula (I) (trade name: Amesolve Red A, manufactured by American Dyestuff Corporation).

Evaluation

The prepared photoreceptors in Examples 1 to 24 and Comparative Examples 1 to 4 were attached to a unit of a digital copier (model: MX-B455W, manufactured by SHARP CORPORATION) remodeled for tests, and electrical properties and light exposure were evaluated.

Electrical Property (Sensitivity)

The developing device was removed from the copier, and, instead of the developing device, a surface electrometer (MODEL 344, manufactured by Trek JAPAN) was installed at the developing site. Under an environment of a temperature of 25° C. and a relative humidity of 50%, a surface potential of the photoreceptor without exposure was adjusted to −600 V, and in this state, a surface potential VL (−V) of a black area was measured.

From the obtained results, the sensitivity was evaluated according to the following criteria.

Criteria

A: VL(−V)<80

Available without any trouble even in a high-speed multifunction peripheral or printer required to have high sensitivity.

B: 80≤NT (−V)<110

Available without any trouble in a low to middle speed multifunction peripheral or printer.

C: 110≤VL(−V)<140

Available without any trouble despite having a slightly thin density in a case of a low-speed and low-price multifunction peripheral or printer.

D: 140≤VL(−V)

Having a low density due to low sensitivity, and problematic in actual use.

Light Exposure Evaluation

The photoreceptor surface excluding a part was masked with black paper, the unmasked part was irradiated light of a white fluorescent lamp having a light intensity of 400 Lux for 5 minutes, and then left, for 5 minutes, and a halftone image was confirmed.

The obtained image was evaluated according to the following criteria.

Criteria

VG: No difference between the irradiated site and the non-irradiated site

G: Slight difference between the irradiated site and the non-irradiated site, but no significant difference NB: Some difference between the irradiated site and the non-irradiated site, but no problem in actual use B: Significant difference between the irradiated site and the non-irradiated site, and problematic in actual use Overall Evaluation On the basis of the evaluation results, the photoreceptor was subjected to overall evaluation according to the following criteria.

VG: rated as "VG" in all items

G: rated as "G" or higher in all items despite including G grade in any items, and available without any trouble unless the multifunction peripheral or printer is high image quality type.

NB: rated as "NB" or higher in all items despite including NB grade in any items, and available without any trouble as long as the multifunction peripheral or printer is low price.

B: rated as "B" in any items, and unavailable in practice.

The compositions and evaluation results of the prepared photoreceptors are presented in Tables 1 and 2.

TABLE 1

| | Composition of photoreceptor | | | | | |
|---|---|---|---|---|---|---|
| | | Charge transporting layer | | | | Protective layer |
| | Light absorbing compound | Charge transporting substance | Film thickness (nm) | Light absorbing compound | | Film thickness (nm) |
| | | | | Amount (g) | Ratio (% by mass)$^{(3)}$ | |
| Example 1 | A$^{(1)}$ | Compound (1) | 36 | 1.15 | 0.18 | — |
| Example 2 | | | 36 | 4.38 | 0.70 | — |
| Example 3 | | | 26 | 1.15 | 0.18 | — |
| Example 4 | | | 36 | 0.31 | 0.05 | — |
| Example 5 | | | 36 | 9.5 | 1.5 | — |
| Example 6 | | | 36 | 0.25 | 0.04 | — |
| Example 7 | | | 36 | 10.1 | 1.6 | — |
| Example 8 | | | 18 | 9.5 | 1.5 | — |
| Example 9 | | | 42 | 0.31 | 0.05 | — |
| Example 10 | | | 17 | 9.5 | 1.5 | — |
| Example 11 | | | 44 | 0.31 | 0.05 | — |
| Example 12 | | | 30 | — | — | 4.5 |
| Example 13 | | | 30 | — | — | 4.5 |
| Example 14 | | | 80 | — | — | 5.5 |
| Example 15 | | | 30 | — | — | 4.5 |
| Example 16 | | | 30 | — | — | 4.5 |
| Example 17 | | | 30 | — | — | 4.5 |
| Example 18 | | | 30 | — | — | 4.5 |
| Example 19 | | | 30 | — | — | 3 |
| Example 20 | | | 30 | — | — | 7 |
| Example 21 | | | 30 | — | — | 2 |
| Example 22 | | | 30 | — | — | 8 |
| Example 23 | | | 30 | 1.15 | 0.18 | 4.5 |
| Example 24 | | TPD$^{(2)}$ | 36 | 1.15 | 0.18 | — |

| | Protective layer | | Evaluation | | |
|---|---|---|---|---|---|
| | Light absorbing compound | | | Light exposure Evaluation | Overall evaluation |
| | Amount (g) | Ratio (% by mass)$^{(4)}$ | Electric property | | |
| | | | VL (−V) | Evaluation | |
| Example 1 | — | — | 68 | VG | VG | VG |
| Example 2 | — | — | 78 | VG | VG | VG |
| Example 3 | — | — | 64 | VG | VG | VG |
| Example 4 | — | — | 60 | VG | G | G |
| Example 5 | — | — | 104 | G | VG | G |
| Example 6 | — | — | 59 | VG | NB | NB |
| Example 7 | — | — | 125 | NB | VG | NB |
| Example 8 | — | — | 95 | G | G | G |
| Example 9 | — | — | 104 | G | G | G |
| Example 10 | — | — | 87 | G | NB | NB |
| Example 11 | — | — | 122 | NB | G | NB |
| Example 12 | 9.05 | 1.2 | 62 | VG | VG | VG |
| Example 13 | 29.40 | 3.8 | 77 | VG | VG | VG |
| Example 14 | 9.05 | 1.2 | 68 | VG | VG | VG |
| Example 15 | 3.00 | 0.4 | 57 | VG | G | G |

TABLE 1-continued

| | | | | | | |
|---|---|---|---|---|---|---|
| Example 16 | 54.30 | 6.8 | 102 | G | VG | G |
| Example 17 | 1.50 | 0.2 | 55 | VG | NB | NB |
| Example 18 | 60.40 | 7.5 | 127 | NB | VG | NB |
| Example 19 | 54.30 | 6.8 | 96 | G | G | G |
| Example 20 | 3.00 | 0.4 | 105 | G | G | G |
| Example 21 | 54.30 | 6.8 | 88 | G | NB | NB |
| Example 22 | 3.00 | 0.4 | 129 | NB | G | NB |
| Example 23 | 9.05 | 1.2 | 72 | VG | VG | VG |
| Example 24 | — | — | 85 | G | G | G |

[1]A: Amesolve Red A,
[2]TPD: Triphenylamine dimer
[3]Ratio to the total solid content in the charge transporting layer,
[4]Ratio to the total solid content in the protective layer

TABLE 2

| | Composition of photoreceptor | | | | | |
|---|---|---|---|---|---|---|
| | Charge transporting layer | | | | | Protective layer |
| | Light absorbing compound | Charge transporting substance | Film thickness (nm) | Light absorbing compound | | Film thickness (nm) |
| | | | | Amount (g) | Ratio (% by mass)[4] | |
| Comparative Example 1 | — | Compound (1) | 36 | — | — | — |
| Comparative Example 2 | HBP[1] | | 36 | 1.15 | 0.18 | — |
| Comparative Example 3 | H[2] | | 36 | 1.15 | 0.18 | — |
| Comparative Example 4 | Y[3] | | 36 | 1.15 | 0.18 | — |

| | Protective layer | | Evaluation | | |
|---|---|---|---|---|---|
| | Light absorbing compound | | Electric property | Light exposure | Overall |
| | Amount (g) | Ratio (% by mass)[5] | VL (−V) | Evaluation | Evaluation | evaluation |
| Comparative Example 1 | — | — | 58 | VG | B | B |
| Comparative Example 2 | — | — | 131 | NB | B | B |
| Comparative Example 3 | — | — | 223 | B | NB | B |
| Comparative Example 4 | — | — | 135 | NB | B | B |

[1]HBP: 2-hydroxy-4-methoxybenzophenone.
[2]H: Amesolve Red H
[3]Y: Amesolve Yellow Y
[4]Ratio to the total solid content in the charge transporting layer.
[5]Ratio to the total solid content in the protective layer The results in Table 1 and Table 2 suggest the followings.

(1) In relation to the electrophotographic photoreceptor having the charge transporting layer and the protective layer, it is found that the photoreceptor containing the perimidine compound according to the present disclosure in both or either one of the charge transporting layer and the protective layer (Examples 1 to 23) has better electric properties and superior external light exposure resistance compared to the photoreceptor without containing the perimidine compound according to the present disclosure (Comparative Example 1), the photoreceptor containing the benzophenone-based UV absorber (Comparative Example 2), the photoreceptor containing the compound described in JP 2012-103333 A (Comparative Example 3), and the photoreceptor containing the compound described in Example 1 of JP H10-048856 A (Comparative Example 4).

(2) From the results of Examples 4 to 7, the amount of the perimidine compound according to the present disclosure added to the charge transporting layer is preferably 0.05 to 1.5% by mass based on the total solid content in the charge transporting layer. If the addition amount is less than 0.05%, the effect on the light resistance is insufficient, and if the addition amount is more than 1.5% by mass, the electric properties deteriorate. This fact and further the results of Examples 1 and 2 indicate that the addition amount is more preferably 0.15 to 0.80% by mass.

(3) From the results of Examples 8 to 12, the film thickness of the charge transporting layer is preferably 18 to 42 µm. If the film thickness is smaller than 18 µm, the effect on the light resistance is insufficient, and if the film thickness is larger than 42 µm, the electric properties deteriorate. This fact and further the results of Examples 1 and 3 indicate that the film thickness is more preferably 25 to 37 µm.

(4) From the results of Examples 15 to 18, the amount of the perimidine compound according to the present disclosure added to the protective layer is preferably 0.3 to 7% by mass based on the total solid content in the protective layer. If the addition amount is less than 0.3%, the effect on the light resistance is insufficient, and if the addition amount is more than 7% by mass, the electric properties deteriorate. This fact and further the results of Examples 12 and 13 indicate that the addition amount is more preferably 1.0 to 4.0% by mass.

(5) From the results of Examples 19 to 22, the film thickness of the protective layer is preferably 3 to 7 µm. If the film thickness is smaller than 3 µm, the effect on the light resistance is insufficient, and if the film thickness is larger than 7 µm, the electric properties deteriorate. This fact and further the results of Examples 12 and 14 indicate that the film thickness is more preferably 4 to 6 µm.

What is claimed is:

1. An electrophotographic photoreceptor comprising, on a conductive base, at least a photoreceptive layer or, alternatively, at least the photoreceptive layer and a protective layer laminated on the photoreceptive layer, wherein
at least one of the photoreceptive layer and the protective layer contains a perimidine compound represented by a general formula (I):

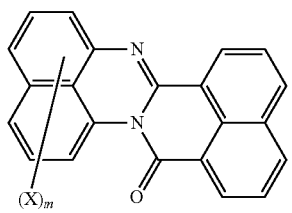

(I)

wherein:
X represents a hydrogen atom, an alkyl group having 1 to 6 carbon atoms, or an alkoxy group having 1 to 6 carbon atoms,
m represents an integer of 1 to 6, a total number of m being 6, a number of the alkyl or alkoxy groups that are potentially present is from 1 to 6, and the rest are the hydrogen atoms,
in a case that the photoreceptive layer contains the perimidine compound,
the photoreceptive layer is a laminated photoreceptive layer in which a charge generating layer containing a charge generating substance and a charge transporting layer containing a charge transporting substance are sequentially laminated from a side of the conductive base, and
the charge transporting layer contains the perimidine compound having a content from 0.18 to 0.70% by mass based on a total solid content of the charge transporting layer, and
in a case that the protective layer contains the perimidine compound, a content of the perimidine compound is 0.3 to 7% by mass based on a total solid content of the protective layer.

2. The electrophotographic photoreceptor according to claim 1, wherein the X represents the hydrogen atom and the m represents 6 in the general formula (I) representing the perimidine compound.

3. The electrophotographic photoreceptor according to claim 1, wherein the charge transporting layer has a film thickness of 18 to 42 µm.

4. The electrophotographic photoreceptor according to claim 1, wherein the protective layer has a film thickness of 3 to 7 µm.

5. A process cartridge comprising at least one selected from the electrophotographic photoreceptor according to claim 1, an electrifier for electrifying the electrophotographic photoreceptor, a developer for developing an electrostatic latent image formed by exposure to form a toner image, and a cleaner for removing a toner remaining on the electrophotographic photoreceptor.

6. An image-forming apparatus comprising at least the electrophotographic photoreceptor according to claim 1, an electrifier for electrifying the electrophotographic photoreceptor, an exposer for exposing the electrified electrophotographic photoreceptor to form an electrostatic latent image, a developer for developing the electrostatic latent image formed by the exposure to form a toner image, a transferer for transferring the toner image formed by the development onto a recording medium, a fuser for fusing the transferred toner image onto the recording medium to form an image, a cleaner for removing and recovering a toner remaining on the electrophotographic photoreceptor, and a charge eliminator for eliminating surface charges remaining on the electrophotographic photoreceptor.

7. An electrophotographic photoreceptor comprising, on a conductive base, at least a photoreceptive layer or, alternatively, at least the photoreceptive layer and a protective layer laminated on the photoreceptive layer,
wherein the protective layer contains a perimidine compound represented by a general formula (I):

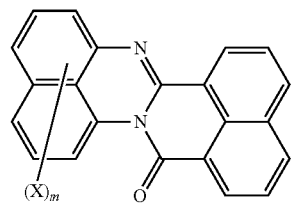

(I)

wherein:
X represents a hydrogen atom, an alkyl group having 1 to 6 carbon atoms, or an alkoxy group having 1 to 6 carbon atoms,
m represents an integer of 1 to 6, a total number of m being 6, a number of the alkyl or alkoxy groups that are potentially present is from 1 to 6, and the rest are the hydrogen atoms, and
a content of the perimidine compound is 0.3 to 7% by mass based on a total solid content of the protective layer.

* * * * *